United States Patent [19]

Olivier et al.

[11] Patent Number: 6,040,483
[45] Date of Patent: Mar. 21, 2000

[54] PROCESS FOR HYDROFORMYLATING OLEFINS

[75] Inventors: Helene Olivier, Rueil Malmaison; Dominique Commereuc, Meudon; Sebastien Drochon, Rueil Malmaison, all of France

[73] Assignee: Institut Francais du Petrole, Rueil Malmaison Cedex, France

[21] Appl. No.: 09/084,352

[22] Filed: May 27, 1998

[30] Foreign Application Priority Data

May 27, 1997 [FR] France ............................. 97 06.570

[51] Int. Cl.$^7$ .................................................. C07C 45/50
[52] U.S. Cl. ........................ 568/454; 568/451; 568/455
[58] Field of Search ................................. 568/454, 451, 568/909, 455, 453, 449

[56] References Cited

U.S. PATENT DOCUMENTS

| | | | |
|---|---|---|---|
| 3,832,391 | 8/1974 | Parshall | 260/497 |
| 4,451,680 | 5/1984 | Knifton | 568/909 |
| 5,105,018 | 4/1992 | Miyazawa et al. | 568/453 |
| 5,874,638 | 2/1999 | Chauvin et al. | 568/454 |

FOREIGN PATENT DOCUMENTS

| | | |
|---|---|---|
| 0 107 430 | 5/1984 | European Pat. Off. . |
| 0 776 880 | 6/1997 | European Pat. Off. . |

OTHER PUBLICATIONS

Chemical Abstracts, vol. 111, No. 3, (23092f), Jul. 1989.

*Primary Examiner*—Shailendra Kumar
*Assistant Examiner*—Sreeni Padmanabhan
*Attorney, Agent, or Firm*—Millen, White, Zelano & Branigan, P.C.

[57] ABSTRACT

Process for liquid-phase hydroformylation of at least one olefin by carbon oxide and hydrogen oxide in the presence of a catalytic composition that contains at least one compound of a transition metal, at least one phosphine oxide, and at least one organic-inorganic salt that does not contain tin or germanium; said salt is a quaternary ammonium salt and/or a quaternary phosphonium salt of general formula $Q^+A^-$, in which $Q^+$ represents an ammonium and/or a quaternary phosphonium and $A^-$ represents an anion. The process applies in particular to internal olefins.

18 Claims, No Drawings

PROCESS FOR HYDROFORMYLATING OLEFINS

CROSS-REFERENCE TO RELATED APPLICATION

This application is related to commonly assigned application Ser. No. 08/755,853 entitled "PROCESS FOR HYDROFORMYLATION OF OLEFINIC COMPOUNDS" filed Feb. 12, 1996, by Chauvin, Olivier, Mussmann (Attorney Docket No. PET 1402), said related application and its French counterpart priority application 95/14.174 filed Nov. 30, 1995, being incorporated by reference herein.

FIELD OF THE INVENTION

The object of this invention is a new process for hydroformylating olefins and in particular internal olefins by carbon oxide and hydrogen oxide; in this process the catalytic system is a solution of at least one compound of a transition metal in an organic-inorganic non-aqueous ionic salt that is liquid at the reaction temperature, and the products that come from the hydroformylation reaction are sparingly soluble or are insoluble.

BACKGROUND OF THE INVENTION

Hydroformylation of olefinic compounds is a reaction of great industrial importance, and most of the processes employ catalysts that are dissolved in an organic phase that consists of reagents, products, and optionally excess ligands, even though problems arise in separating and recovering the catalyst, in particular when the latter is a noble metal, such as, for example, rhodium.

A solution for this problem was described in French Patent FR-2,314,910. The solution consists in carrying out the hydroformylation in the presence of an aqueous solution that contains a rhodium complex that is made water-soluble thanks to the presence of a sulfonated phosphine ligand which is itself water-soluble, such as the sodium salt of trisulfonated triphenylphosphine. In this way, the organic phase that contains the aldehydes is easily separated from the aqueous phase that contains the catalyst. The technique is the object of a considerable number of works that were discussed in an article by W. A. Herrmann that appeared in Angewandte Chemie International [Applied Chemistry International] in 1993, Volume 32, pages 1524 ff. Despite the great industrial advantage of this technique for hydroformylating propylene, a drawback of this two-phase system is that olefins are not soluble in water; this leads to relatively low reaction rates which make it impossible to use it for long-chain olefins.

Further described in U.S. Pat. No. 3,565,823 was a technique that consists in dispersing a compound of a transition metal in a tin salt or germanium salt and an ammonium salt or a quaternary phosphonium salt of formula $(R_1R_2R_3R_4Z)YX_3$, in which $R_1$, $R_2$, $R_3$, and $R_4$ are hydrocarbyl radicals that have up to 18 carbon atoms, Z is nitrogen or phosphorus, Y is tin or germanium, and X is a halogen, chlorine, or bromine, whereby this ionic-type non-aqueous medium constitutes a "molten salt." U.S. Pat. No. 3,657,368 described a process for hydrogenating olefins, and U.S. Pat. No. 3,919,271 described a process for hydrogenating nitriles that uses the preceding composition both with a tin and a germanium base. U.S. Pat. No. 3,832,391 claimed a process for carbonylating olefins by the same composition.

The compositions described above suffer from the drawback of having a relatively high melting point, while the hydroformylation reaction takes place at, for example, less than 90° C.

French Patent Application No. 95/14147 of Nov. 30, 1995 proposed that it was possible both to keep the advantages of a two-phase application while avoiding the drawbacks that are associated with, on the one hand, the use of water and, on the other, with the use of compounds with a high melting point, by dissolving the catalytic compounds of transition metals of groups 8, 9, and 10 and in particular the compounds of cobalt, ruthenium, rhodium, iridium, palladium, and platinum, which are known for catalyzing hydroformylation, in organic-inorganic salts that are liquid at low temperature.

SUMMARY OF THE INVENTION

It has now been found that adding phosphine oxide to the preceding catalytic composition made it possible to carry out the hydroformylation of olefins and in particular internal olefins, with good levels of activity and selectivity, into aldehydes.

More specifically, the invention has as its object a process for the liquid-phase hydroformylation of olefins (or compounds that are olefinically unsaturated) and in particular internal olefins, in which process the reaction is carried out in the presence of at least one phosphine oxide and an organic-inorganic salt of general formula $Q^+A^-$, in which $Q^+$ represents a quaternary ammonium and/or quaternary phosphonium and $A^-$ represents an anion, whereby said salt does not contain tin or germanium, and at least one compound of a transition metal (groups 8, 9, and 10).

The liquid salts according to the invention have the general formula $Q^+A^-$, in which $Q^+$ represents a quaternary ammonium and/or a quaternary phosphonium and A represents any anion that is known as being non-coordinating and being able to form a liquid salt at low temperature, i.e., below 150° C. and advantageously below 90° C., and preferably at most 85° C., and preferably at most 50° C., such as preferably tetrafluoroborate, hexafluorophosphate, hexafluoroantimonate, hexafluoroarsenate, trifluoromethylsulfonate, and fluorosulfonate ions. It is also possible to use the dichlorocuprate, tetrachloroborate, tetrachloroaluminate, and trichlorozincate anions, but this is not preferred. It is preferred to exclude the halides. The quaternary ammonium and/or quaternary phosphonium preferably correspond to general formulas $NR^1R^2R^3R^{4+}$ and $PR^1R^2R^3R^{4+}$ or to general formulas $R^1R^2N=CR^3R^{4+}$ and $R^1R^2P=CR^3R^{4+}$, where $R^1$, $R^2$, $R^3$, $R^4$, which are identical or different, represent hydrogen, with the exception of cation $NH_4+$, and preferably a single substituent can represent hydrogen, or hydrocarbonyl radicals that have 1 to 12 carbon atoms, for example, alkyl groups that are saturated or unsaturated, cycloalkyl or aromatic, aryl or aralkyl, and that comprise 1 to 12 carbon atoms. The ammonium and/or phosphonium can also be derived from heterocycles that contain nitrogen or phosphorus and that contain 1, 2 or 3 nitrogen atoms and/or phosphorus atoms, of general formula:

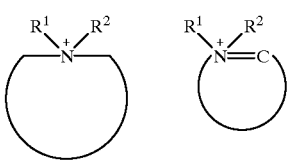

-continued

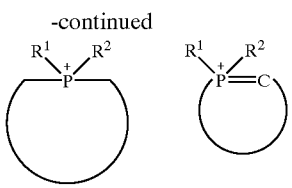

in which the cycles consist of 4 to 10 atoms, preferably 5 to 6 atoms, whereby $R^1$ and $R^2$ are defined as above. The quaternary ammonium or quaternary phosphonium can also be a cation of formula:

$$R^1R^{2+}N=CR^3-R^5-R^3C=N^+R^1R^2$$

$$R^1R^{2+}P=CR^3-R^5-R^3C=P^+R^1R^2$$

in which $R^1$, $R^2$, and $R^3$, which are identical or different, are defined as above and $R^5$ represents an alkylene or phenylene radical. Among groups $R^1$, $R^2$, $R^3$ and $R^4$, the radicals methyl, ethyl, propyl, isopropyl, butyl, sec-butyl, tert-butyl, amyl, methylene, ethylidene, phenyl, or benzyl will be mentioned; $R^5$ can be a methylene, ethylene, propylene, or phenylene group. The ammonium cation and/or phosphonium cation is preferably selected from the group that is formed by N-butylpyridinium, N-ethylpyridinium, butyl-3 methyl-1 imidazolium, diethylpyrazolium, ethyl-3 methyl-1 imidazolium, pyridinium, trimethylphenylammonium, and tetrabutylphosphonium. Likewise, $A^-$ is tetrafluoroborate providing that $Q^+$ represent quaternary ammonium or anion $A^-$ is selected from the group consisting of hexafluorophosphate, hexafluoroantimonate, hexaflouroarsenate, flourosulphonate, bis-perfluoroalkysulphonyl amides, perfluoroalkyl sulphonates, dichlorocuprate, tetrachloroborate, tetrachloroaluminate, and trichlorozincate. As examples of salts that can be used according to the invention, it is possible to cite N-butylpyridinium hexafluorophosphate, N-ethyl pyridinium tetrafluoroborate, tetrabutylphosphonium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, and trimethylphenylammonium hexafluorophosphate. These salts can be used alone or in a mixture. They act as solvents. Butyl-3-methyl-1-imidazolium dichlorocuprate, pyridinium tetrachloroborate, butyl-3-methyl-1-imidazolium tetrachloroaluminate, and butyl-3-methyl-1-imidazolium trichlorozincate can also be used.

The compounds of the transition metals that can be used according to the invention are generally all the compounds of the transition metals of groups 8, 9, and 10 and particularly those that are known to one skilled in the art for hydroformylating olefins. They can be used alone or in a mixture. They can be complexed or linked to an organic ligand. They can be used in the form of salts, and in a preferred way, which is not a halide. These are, among others, compounds of cobalt, rhodium, iridium, ruthenium, palladium, and platinum. The selection of the catalytic compound of the transition metal is not critical. For example, $HRh(CO)(PR_3)_3$, $HRh(CO)_2(PR_3)$, $HRh(CO)[P(OR)_3]_3$, $Rh(acac)(CO)_2$ (where acac means acetylacetonate), $Rh_6(CO)_{16}$, $[Rh(norbornadiene) (PPh_3)_2]^+ [PF_6]^-$, $[Rh(C)_3(PPh_3)_2]^+[BPh_4]^-$, $RhCl (CO)(PEt_3)_2$, $[RhCl (cyclooctadiene)]_2$, $[Rh(CO)_3(PR_3)_2]^+BPh_4^-$, $[Rh(CO)_3 (PR_3)_2]^+PF_6^-$, $HCo(CO)_4$, $RU_3(CO)_{12}$, $[RuH(CO) (acetonitrile)_2(PPh_3)_3$ $^+[BF_4]^-$, $PtCl_2(cyclooctadiene)$, $[Ir (CO)_3(PPH_3)]^+[PF_6]^-$, $[HPt(PEt_3)_3]^+[PF_6]$ will be mentioned. It is also possible, however, to employ totally inorganic salts, catalyst precursors, such as $RH_2O_3$, $Pd(NO_3)_2$ and $Rh(No_3)_3$, and in a nonpreferred way halides such as $RhCl_3, 3H_2O$.

The phosphine oxides according to the invention have the general formula $R_1R_2R_3PO$, in which $R_1$, $R_2$, and $R_3$, which are identical or different, represent hydrocarbyl groups that preferably have 1 to 12 carbon atoms, for example, alkyl groups, saturated or unsaturated, cycloalkyl or aromatic, aryl or aralkyl, that contain 1 to 12 carbon atoms. These ligands can be mono-dentate or bi-dentate. They can also carry another group such as amine, ammonium, alcohol, carboxylic acid or sulfonate. The catalytic composition is obtained by mixing, in any way, liquid salt with the compound of the transition metal and optionally the ligand.

The organic ligand-transition metal catalytic complexes can be prepared outside of the reaction medium and are introduced into said medium for reaction. They can also be formed in situ, in the reaction medium, by introducing the components that are required for their formation.

Another advantage that is associated with the process of this invention lies in the fact that it is possible to use a wide variety of ligands that are not compatible with water but that are stable in these media, such as, for example, phosphites, which are very easy to hydrolyze and are much easier to synthesize than phosphines.

In general, the catalytic composition can contain a miscible or partially miscible organic solvent such as an aromatic hydrocarbon and/or a nonmiscible aliphatic hydrocarbon which makes possible better separation of phases. Preferably, the catalytic composition does not contain water.

The concentration of the transition metal compound (preferably of the complex) in the "molten salt" is not critical. It is advantageously between 1 mmol of compound per liter of "molten salt" and 500 mmol per liter, preferably between 2 and 200 mmol per liter, and again between 2 and 100, and even 2 to 50. The molar ratio between the organic ligand and the compound of the transition metal can be between 1 and 100, preferably between 1 and 20.

The components that are part of the composition according to the invention can be mixed in any order at a temperature that is between $-20°$ C. and $+200°$ C., and preferably 30° C. to less than 150° C., and advantageously from 0° C. to less than 150° C., 0°C. to 120° C., or else 0 to less than 90° C., preferably 0–85° C. or 0 to 50° C.

The olefinically unsaturated compounds that can be hydroformylated according to the invention are the internal monoolefins. As an example, it is possible to cite the hydroformylation of butene-2 into pentanal and isopentanals, pentenes into hexanal and isohexanals, hexenes into isoheptanals, and isooctenes into isononanals. These compounds can be used in pure form or may be diluted with saturated or unsaturated hydrocarbons.

The partial-pressure ratio of carbon monoxide to hydrogen that is used in the reaction medium for hydroformylation can be from 1:10 to 10:1, and preferably 1:1, but any other ratio may be used according to the implementation of the process.

The temperature at which the hydroformylation is carried out will be between 30° C. and 200° C.; advantageously the temperature is less than 150° C., preferably between 50° C. and less than 150° C., preferably less than 90° C., and still more advantageously at most 85° C. A preferred temperature range is between 50° C. and less than 150° C. and still more advantageously from 30° C. to 120° C., from 30° C. to less than 90° C. The pressure can be between 1 MPa and 20 MPa, preferably between 2 MPa and 10 MPa.

The catalytic reaction for hydroformylation of internal olefins may be carried out in a closed system, a semi-open system, or continuously with one or more reaction stages. At the outlet of the reactor, the organic phase that contains the reaction products (aldehydes) is advantageously separated by simple decanting of the catalytic polar phase that contains the "molten salt" and the majority of the catalyst. The polar phase that contains at least part of the catalyst is, at least in part, returned to the reactor, whereby the remainder is treated to eliminate the residues of the catalyst.

The following examples illustrate the invention without limiting its scope:

EXAMPLE 1

4 mL of butylmethylimidazolium hexafluorophosphate, 19.3 mg (0.075 mmol) of the Rh(acetylacetonate) $(CO)_2$ complex, and 197 mg (0.71 mmol) of triphenylphosphine oxide that is dissolved in 2 mL of toluene, 2 mL of heptane (standard), and 7.5 mL (68 mmol) of 2-pentene were introduced into a double-jacket stainless steel reactor with a 100 mL capacity that is purged of air and moisture and placed under the atmospheric pressure of the hydrogen-carbon oxide mixture. The pressure of the hydrogen-carbon oxide mixture was raised to 5 MPa and the temperature to 80° C., and stirring was initiated. After 2 hours, stirring was halted, and the mixture was decanted; the supernatant organic phase, which was very light in color, was drawn off. The conversion of 2-pentene was more than 80%. The molar output was 17% of hexanal and 65% of 2-methylpentanal. The remainder consisted of 2-pentene and traces of 1-pentene (<1%).

EXAMPLE 2 (comparative)

The operation was carried out with the set-up described in Example 1. 19.3 mg (0.075 mmol) of the Rh(acetylacetonate $(CO)_2$ complex and 197 mg (0.71 mmol) of triphenylphosphine oxide that was dissolved in 7.5 mL of toluene, 20 ml of heptane, and 7.5 mL (68 mmol) of 2-pentene were introduced. The pressure of the hydrogen-carbon oxide mixture was raised to 5 MPa and the temperature to 80° C., and stirring was initiated. After 2 hours, stirring was halted, degassing was done, and the organic phase was drawn off. The conversion of the 2-pentene was 30%, and the aldehyde selectivity was 99%, whereby the remainder was 1-pentene.

The preceding examples can be repeated with similar success by substituting the generically or specifically described reactants and/or operating conditions of this invention for those used in the preceding examples.

The entire disclosure of all applications, patents and publications, cited above, and of corresponding French application No. 97/06570, are hereby incorporated by reference.

From the foregoing description, one skilled in the art can easily ascertain the essential characteristics of the invention, and without departing from the spirit and scope thereof, can make various changes and modifications of the invention to adapt it to various usages and conditions.

We claim:

1. A process comprising conducting a liquid-phase hydroformylation of at least one internal olefin by carbon monoxide and hydrogen in the presence of a catalytic composition that contains at least one compound of a transition metal other than ruthenium, a phosphorous-containing ligand consisting essentially of at least one phosphine oxide of the formula $R_1R_2R_3PO$ wherein $R_1$ $R_2$ and $R_3$ being identical or different represent hydrocarbyl of 1–12 carbon atoms, and at least one organic-inorganic salt that does not contain tin or germanium; said salt is at least one quaternary ammonium salt and/or at least one quaternary phosphonium salt of general formula $Q^+A^-$, in which $Q^+$ represents an ammonium and/or a quaternary phosphonium and $A^-$ represents an anion wherein $A^-$ is tetrafluoroborate providing that $Q^+$ represent quaternary ammonium or anion $A^-$ is selected from the group consisting of hexafluorophosphate, hexafluoroantimonate, hexafluoroarsenate, fluorosulphonate, bis-perfluoroalkylsulphonyl amides, perfluoroalkyl sulphonates, dichlorocuprate, tetrachloroborate, tetrachloroaluminate, and trichlorozincate so as to produce selectively aldehydes at high conversion rates of said internal olefins in an organic phase, and to produce a polar phase containing at least part of the catalyst.

2. Process according to claim 1, wherein anion $A^-$ is selected from the group consisting of tetrafluoroborate, hexafluorophosphate, hexafluoroantimonate, hexafluoroarsenate, trifluoromethylsulfonate, fluorosulfonate, else dichlorocuprate, tetrachloroborate, tetrachloroaluminate, and trichlorozincate.

3. A process according to claim 1, wherein the quaternary ammonium cation and/or quaternary phosphonium cation are selected from the group that is formed by the cations of general formula:

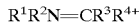

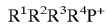

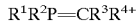

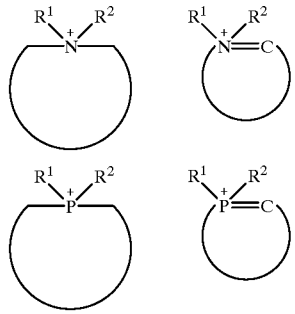

wherein $R^1$, $R^2$, $R^3$, and $R^4$, which are identical or different, represent hydrogen, with the exception of $NH_4^+$, and hydrocarbyl radicals that have 1 to 12 carbon atoms, and wherein the cycles are constituted of 4 to 10 atoms.

4. A process according to claim 1, wherein the quaternary ammonium cation and/or quaternary phosphonium cation have for general formulas:

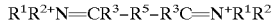

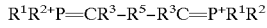

in which $R^1$, $R^2$, and $R^3$, which are identical or different, represent hydrogen or hydrocarbyl radicals that have 1 to 12 carbon atoms and $R^5$ represents an alkylene or phenylene radical.

5. A process according to claim 1, wherein the quaternary ammonium cation and/or quaternary phosphonium cation are selected from the group consisting of N-butylpyridinium, N-ethylpyridinium, butyl-3 methyl-1 imidazolium, diethylpyrazolium, ethyl-3 methyl-1 imidazolium, pyridinium, trimethylphenylammonium, and tetrabutylphosphonium.

6. A process according to claim 1, wherein the quaternary ammonium salts and/or quaternary phosphonium salts are selected from the group consisting of N-butylpyridinium hexafluorophosphate, N-ethyl pyridinium tetrafluoroborate, tetrabutylphosphonium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, trimethylphenylammonium hexafluorophosphate, butyl-3 methyl-1 imidazolium dichlorocuprate, pyridinium tetrachloroborate, butyl-3 methyl-1 imidazolium tetrachloroaluminate, and butyl-3 methyl-1 imidazolium trichlorozincate.

7. A process according to claim 1, wherein the transition metal is cobalt, rhodium, iridium, palladium, and platinum.

8. A process according to claim 1, wherein the transition metal compound is a transition metal complex.

9. A process according to claim 1, wherein the compound of the transition metal is selected from the group consisting of $HRh(CO)(PR_3)_3$, $HRh(CO)_2(PR_3)$, $HRh(CO)-[P(OR)_3]_3$, $Rh(acac)(CO)_2$ (where acac means acetylacetonate) $Rh_6(CO)_{16}$, $[Rh(CO)_3(PPh_3)_2]^+[BPh_4]^-$, $RhCl(CO)(PEt_3)_2$, $[RhCl(cyclooctadiene)]^2$, $[Rh(CO)_3(PR_3)_2]^+BPh_4^-$, $[Rh(CO)_3(PR_3)_2]^+PF_6^-$, $[Rh(norbornadiene)(PPh_3)_2^+[PF_6]^-$, $HCo(CO)_4$, $(acetonitrile)_2(PPh_3)_3^+[BF_4]^-$, $PtCl_2$ (cyclooctadiene), $[Ir(CO)_3(PPH_3)]^+[PF_6]^-$, $[HPt(PEt_3)_3]^+[PF_6]^-$, $Rh_2O_3$, $Pd(NO_3)_2$ and $Rh(NO_3)_3$.

10. A process according to claim 1, wherein the phosphine oxide contains at least one amine, ammonium, alcohol, carboxylic-acid, or sulfonate group.

11. A process according to claim 1, wherein the concentration of the compound or compounds of the transition metal or transition metals relative to the ammonium salt and/or phosphonium salt is 1 to 500 mmol per liter.

12. A process according to claim 1, wherein the catalytic composition also contains an organic solvent.

13. A process according to claim 12, wherein the solvent is selected from the group consisting of aromatic hydrocarbons and aliphatic hydrocarbons.

14. A process according to claim 1, wherein the organic phase that contains the aldehydes is separated from the polar phase, whereby said polar phase contains at least a portion of the catalyst and at least partly recycling said polar phase into the hydroformylation reactor.

15. A process according to claim 1 operating between 30 and 200° C., under a total pressure of between 1 MPa and 20 MPa, whereby the partial-pressure ratios of carbon monoxide to hydrogen are 1:10 to 10:1.

16. A process according to claim 1, wherein the transition metal is rhodium.

17. A process according to claim 5, wherein the transition metal is rhodium.

18. A process according to claim 6, wherein the transition metal is rhodium.

* * * * *